United States Patent [19]

Thurn-Müller et al.

[11] Patent Number: 5,310,578
[45] Date of Patent: May 10, 1994

[54] DEPOSITION OF COSMETICALLY FUNCTIONAL MATERIAL ONTO PIGMENTS AND FILLERS

[75] Inventors: Angelika Thurn-Müller, Frankenthal, Fed. Rep. of Germany; Jane Hollenberg, New York; Ian Scott, Scarsdale, both of N.Y.

[73] Assignee: Merck Patent Gesellschaft, Darmstadt, Fed. Rep. of Germany

[21] Appl. No.: 583,383

[22] Filed: Sep. 17, 1990

[51] Int. Cl.$^5$ ............................ B05D 7/00; C08J 7/00
[52] U.S. Cl. ............................ 427/220; 106/414; 106/415; 106/429; 106/436; 106/450; 106/460; 106/504; 252/314; 424/5g310; 514/275; 514/387; 514/473; 514/475; 514/873
[58] Field of Search .................... 424/59, 60; 427/220; 514/275, 473, 475, 873, 387; 106/414, 415, 429, 436, 450, 460, 504; 252/313.1, 314

[56] References Cited

U.S. PATENT DOCUMENTS

| | | | |
|---|---|---|---|
| 4,390,524 | 6/1983 | Nasuno et al. | 424/63 |
| 4,551,330 | 11/1985 | Wagman et al. | 252/309 X |
| 4,622,074 | 11/1986 | Miyoshi et al. | 106/308 F |
| 4,648,908 | 3/1987 | Takasuka et al. | 106/308 F |
| 4,882,225 | 11/1989 | Fukui et al. | 427/220 X |
| 4,976,953 | 12/1990 | Orr et al. | 252/DIG. 5 |
| 5,015,469 | 5/1991 | Yoneyama et al. | 252/174.15 X |
| 5,039,513 | 8/1991 | Chatterjee et al. | 252/106 X |

FOREIGN PATENT DOCUMENTS 209391 5/1984 Fed. Rep. of Germany.

*Primary Examiner*—Michael Lusignan
*Attorney, Agent, or Firm*—Milen, White, Zelano, & Branigan

[57] ABSTRACT

A process for coating the surface of pigment and filler particles with an oleaginous and cosmetically functional material, characterized in that an aqueous suspension of the pigment or filler is mixed with an emulsion of said oleaginous material to be coated onto the surface of pigment or filler particles, followed by adding a component capable of breaking the emulsion to the thus obtained mixture, whereby the emulsified material coalesces onto the surface of the pigment or filler particles. The thus obtained pigments or fillers exhibit excellent properties when used in cosmetics.

12 Claims, No Drawings

DEPOSITION OF COSMETICALLY FUNCTIONAL MATERIAL ONTO PIGMENTS AND FILLERS

BACKGROUND OF THE INVENTION

The invention relates to a process for coating the surface of pigment or filler particles with an oleaginous and cosmetically functional material.

The coating of pigments for general use in cosmetics is well known in the art. On the one hand, materials are deposited on the pigment surface from aqueous or nonaqueous solutions of said materials via conversion of the materials to insoluble salts as disclosed, for example in U.S. Pat. No. 4,648,908 and dispersing the pigments in solutions of the materials to be deposited, followed by filtering off of the pigments so coated with a film of said materials being adhered to the pigment particle surface.

The coating of oleaginous and cosmetically functional materials onto the surface of pigment particles is also known. Thus, a simple mixing of the components as well as a suspending of the pigments in a solution of the materials to be deposited, followed by separating the solvent, have been done. This is described, for example, in U.S. Pat. No.4,390,524 and DD 209391.

Other known methods relate to depositions via precipitation or adhesion of water-soluble or water-suspendable materials, respectively, onto the surface of pigment particles. U.S. Pat. No.4,622,074 describes a method for uniformly coating the surface of pigments or extender pigments with hydrogenated lecithin via adsorption of a water-insoluble salt. It is further indicated in this patent that it is not possible to coat a pigment with lecithin itself because lecithin is an oily substrate.

The disadvantages of the known processes are as follows: incomplete deposition and dispersion of the oleaginous material onto the particle surface of pigments by simple mixing of the components, and complicated derivatization of natural oily substrates needed to circumvent the coating problem as indicated above for lecithin.

Whenever oleaginous and water-insoluble materials have to be deposited a fundamental disadvantage is the necessary use of organic solvents. Even though deposition of oleaginous materials from solvents results in pigments having advantageous properties, safety and environmental concerns require the use of costly explosion proof manufacturing equipment with the capability of recycling the solvent.

SUMMARY OF THE INVENTION

The object of the present invention is to provide an improved process for coating pigments and fillers with oleaginous materials for use in cosmetics.

This object is achieved by the present invention. It has been found surprisingly that the surface of pigment or filler particles can be coated with oleaginous and cosmetically functional materials in an advantageous manner when an aqueous suspension of the pigments or fillers to be coated is mixed with an emulsion of said oleaginous materials to be deposited onto the particle surface, followed by coalescing of the material on said particle surface.

The invention accordingly provides a process for coating the surface of pigment or filler particles with an oleaginous and cosmetically functional material, characterized in that an aqueous suspension of the pigment or filler is mixed with an emulsion of said oleaginous material to be coated onto the surface of pigment or filler particles, followed by adding to that mixture a component capable of breaking the emulsion, whereby the emulsified material coalesces onto the surface of the pigment or filler particles.

The invention also provides cosmetic compositions comprising pigments or fillers, the surface of which is coated with an oleaginous and cosmetically functional material, wherein the pigments or fillers being coated with said oleaginous and cosmetically functional material are prepared by a process as above.

The process according to the invention is carried out as follows:

First an aqueous suspension of the pigment or filler to be coated with the oleaginous material is prepared. The preferred concentration of pigment or filler in the slurry varies according to pigment type but is preferably the highest concentration which will remain fluid. For mica pigments, about 25–50 %, preferably about 30 % by weight is optimum, for pigments having lower water adsorption, such as iron oxides, 40–45 % by weight is preferred.

Separately an aqueous dispersion of an emulsifier with a concentration of, in particular, about 10 % by weight is prepared in which the oleaginous and cosmetically functional material is emulsified hereafter. The concentration of the oleaginous material to be deposited is preferably equal to or greater than that of the emulsifier. Then the pigment suspension and the thus prepared emulsion are mixed together. Preferably the above emulsion is added to the pigment suspension under vigorous stirring. The final concentration of the coating (oleaginous material plus emulsifier) is preferably to be in the range of 0.5–10 % by weight of pigment or filler to be coated.

Thereupon a component is added to the thus prepared dispersion which is capable of breaking the emulsion, thereby causing coalescence of the oleaginous material onto the surface of pigment or filler particles.

Finally, the so-coated pigments are isolated and dried by conventional methods, for example by filtration, tray drying, spray drying or fluidized bed drying.

The pigments or fillers which can be coated with an oleaginous and cosmetically functional material according to the invention are inorganic or organic substrates. Non-limiting examples of such pigments or fillers are titanium dioxide, zinc oxide, zirconium dioxide, red iron oxide, yellow iron oxide, black iron oxide, ultramarine blue, Prussian blue, chromium oxide, chromium hydroxide, talc, kaolin, muscovite mica, sericite, other micas, magnesium carbonate, calcium carbonate, aluminum silicate, magnesium silicate, calcium silicate, clay, titanated mica, bismuth oxychloride, silica beads, or plastic beads, such as acrylates, synthetic organic colorants, and natural colorants. Platelet-like substrates are preferred.

The preferred particle size range of the pigments or fillers to be coated is from below 5 $\mu$m to about 50 $\mu$m. In particular, for the best skin feel, the particle size is smaller than 15 $\mu$m.

Emulsifiers that are suitable for the process according to the invention are ionic in nature, capable of being precipitated by di- or trivalent metal salts. Examples are (but not limited to) phosphates (for example, diethanolamine (DEA) cetyl phosphate, polyoxyethylene-3 oleyl ether phosphate), carboxylates (for example, Na ceteth- 13 carboxylate, Na isosteareth-11 carboxylate) and glutamates (for example, Na myristoyl glutamate).

The oleaginous material to be deposited by a process according to the invention may be selected from the group consisting of fat-soluble vitamins, sun screens, emollients (skin protectants) and other oily materials, e.g., those mentioned in U.S. Pat. No. 4,390,524. Non-limiting examples of compounds are vitamin A, vitamin A palmitate, vitamin D, vitamin E, vitamin E acetate, padimate O (ethyl hexyl dimethyl p-aminobenzoic acid, 3-(4-methyl)benzylidene camphor, squalene, isostearyl stearoyl stearate, maleated soybean oil, isostearyl isostearate, wheat germ oil, avocado oil and jojoba oil.

Components which are capable of breaking the emulsion are per se known in the art. Examples therefore are di- or trivalent metal salts such as magnesium sulphate or aluminum ammonium sulphate. In the process, preferably a solution of the di- or trivalent metal salt is added to the pigment suspension/emulsion dispersion to break the emulsion.

Alternatively, the emulsion can be broken by pH adjustment, i.e., the pH of the above dispersion is changed by addition of an acidic or basic solution to a pH value by which the emulsifier itself precipitates. Acidic solutions are added to precipitate anionic emulsifiers; basic solutions are added to precipitate cationic emulsifiers. Such methods of breaking emulsions are conventional.

The process according to the invention clearly shows several advantages. On the one hand all oleaginous materials without any limitation can be deposited onto the surface of pigment or filler particles in the absence of organic solvents. In addition, as a rule, the pigments or fillers prepared by a process according to the invention are completely encapsulated with the oleaginous material. This result is not always achieved by means known in the art, e.g., by spraying the coating materials onto the powder bulk without solvent.

Thus, the pigments prepared according to the invention have a skin feel as well as a powder compressibility superior to pigments prepared by the above-mentioned spraying method.

The pigments prepared according to the process of the invention exhibit excellent cosmetic properties such as improved skin feel and compressibility of powders. The process allows the incorporation of further skin treatment functionality, for example, moisturization, antioxidant and UV screening. With deposition of, for example, vitamin E acetate, pigments for cosmetic use containing a free radical scavenger could be made.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, are hereby incorporated by reference.

EXAMPLES

Example 1

98.5 g of mica (particle size 1 to 15 $\mu$m) are suspended in 330 g of distilled water. To this slurry, an emulsion concentrate consisting of 7.5 g of a 10 % aqueous solution of DEA cetyl phosphate (Amphisol, commercially available from Givaudan, Geneva, Switzerland) and 0.75 g of vitamin E acetate as the oleaginous material is added with continuous agitation. After stirring for several minutes at room temperature, 4 g of a 0.M AlNH$_4$(SO$_4$)$_2$ are added slowly to break the emulsion. The emulsified vitamin E acetate coalesces onto the mica surface. The coated pigment is then filtered off and dried by spray drying. The pigment offers the added benefit of carrying a skin treatment component, vitamin E acetate, a scavenger of free radicals which have been implicated in the destructive chemical reactions that degrade the skin's structure.

Example 2

The procedure is analogous to that of Example 1 but 0.75 g of vitamin A palmitate is used as the oleaginous material. The pigment offers the added benefit of carrying a skin treatment component, vitamin A palmitate. Vitamin A and its derivatives have been shown to reduce the visible signs of photoaging of the skin. Example 3

96 g of talc (particle size 1 to 15 $\mu$) are suspended in 330 ml of distilled water. To this slurry an emulsion concentrate consisting of 20 g of a 10 % aqueous solution of DEA cetyl phosphate and 2 g of 3-(4-methylbenzylidene)-camphor (Eusolex 6300, commercially available from EM Industries, Hawthorne, New York) as the oleaginous material is used with continuous agitation. After stirring for several minutes at room temperature, 6 g of 0.1 M MgSO$_4$ are added slowly to break the emulsion.

The emulsified camphor derivative coalesces onto the talc surface. The coated pigment is then filtered off and dried by spray drying. The pigment offers the added benefit to the skin of protection against the damaging effects of ultraviolet light.

Example 4

98.75 g of Timiron MP-1005 (titanium dioxide-coated mica, commercially available from Rona, Hawthorne, New York) are suspended in 330 g of distilled water. To this slurry an emulsion concentrate consisting of 5 g of a 10 % aqueous solution of Na-stearoyl glutamate and 0.75 g of Ergocalciferol (vitamin D, commercially available from Hofmann-La Roche, Basel, Switzerland) as the oleaginous material is added with continuous agitation. After stirring for several minutes at room temperature, 6 g of 0.1 M AlNH$_4$(SO$_4$)$_2$ are added slowly to break the emulsion. The emulsified Ergocalciferol coalesces onto the titanated mica surface. The coated pigment is then filtered off and dried by spray drying. The pigment offers the added benefit of delivering vitamin D, known to be essential for maintaining the structural components of the skin.

Example 5

98.5 g of mica (particle size 1 to 15 $\mu$m) are suspended in 330 g of distilled water. To this slurry an emulsion concentrate of 3.5 g of a 20% aqueous solution of Na ceteth-13 carboxylate and 0.75 g of maleated soybean oil as the oleaginous material is added with continuous agitation. After stirring for several minutes at room temperature, 4 g of 0.1 M AlNH$_4$(SO$_4$)$_2$ are added slowly to break the emulsion. The emulsified maleated soybean oil coalesces onto the mica surface.

The coated pigment is then filtered off and dried by spray drying.

The coated pigments according to examples 1-5 exhibit excellent skin feeling and improved compressibility in pressed powder formulations.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for coating the surface of a pigment or filler particle with an oleaginous material, comprising mixing an aqueous suspension of the pigment or filler with an emulsion of water-insoluble oleaginous material and adding a component capable of breaking the emulsion to the thus obtained mixture, whereby the emulsion is broken and the emulsified material coalesces onto the surface of the pigment or filler particles.

2. A process according to claim 1, wherein the pigment or filler to be coated with the oleaginous material is a platelet-like substrate.

3. A process according to claim 2, wherein the pigment or filler is titanium dioxide, zinc oxide, zirconium dioxide, red iron oxide, yellow iron oxide, black iron oxide, ultramarine blue, Prussian blue, chromium oxide, chromium hydroxide, talc, kaolin, muscovite mica, sericite, magnesium carbonate, calcium carbonate, aluminum silicate, magnesium silicate, calcium silicate, clay, titanated mica, bismuth oxychloride, silica beads, or beads of a polymeric material.

4. A process according to claim 1, wherein the oleaginous material to be deposited onto the pigment or filler surface is a fat-soluble vitamin, a sunscreen, a skin protective emollient or a mixture thereof.

5. A process according to claim 4, wherein the oleaginous material is vitamin A, vitamin A palmitate, vitamin D, vitamin E, vitamin E acetate, ethyl hexyl dimethyl p-aminobenzoic acid, 3-(4-methyl)benzylidene camphor, squalene, isostearoyl stearate, maleated soybean oil, isostearyl isostearate, wheat germ oil, avocado oil or jojoba oil.

6. A process according to claim 1, wherein the emulsifier is a phosphate, a carboxylate or a glutamate.

7. A process according to claim 1, wherein the component capable of breaking the emulsion is a di- or trivalent metal salt.

8. A process according to claim 1, wherein the emulsion of water-insoluble oleaginous material is produced by mixing the material with an emulsifier.

9. A process according to claim 8, wherein the emulsifier is a phosphate, carboxylate, or glutamate.

10. In a cosmetic composition comprising a pigment or filler, the surface of which is coated with an oleaginous and cosmetically functional material, the improvement wherein said pigment, or filler is prepared by a process according to claim 1.

11. A process according to claim 1, wherein, after coating with the oleaginous material, the pigment or filler is dried to produce a powder.

12. A pigment or filler coated with an oleaginous material, produced by the process of claim 11.

* * * * *